US005685294A

United States Patent [19]
Gupte et al.

[11] Patent Number: 5,685,294
[45] Date of Patent: Nov. 11, 1997

[54] POWDER INHALER HAVING MAGAZINE STORAGE AND A HINGED MOUTHPIECE

[75] Inventors: Rajaram Arun Gupte, Ingelheim; Erich Hertl, Gilching, both of Germany

[73] Assignee: Boehringer Ingelheim KG, Ingelheim am Rhein, Germany

[21] Appl. No.: 328,294

[22] Filed: Oct. 24, 1994

Related U.S. Application Data

[63] Continuation of Ser. No. 95,029, Jul. 20, 1993, abandoned, which is a continuation of Ser. No. 829,083, filed as PCT/EP90/01336, Aug. 14, 1990, abandoned.

[30] Foreign Application Priority Data

Aug. 27, 1989 [DE] Germany ............... 39 27 170.6

[51] Int. Cl.$^6$ .............. A61M 15/00; A61M 16/00; B05D 7/14; B65D 83/06
[52] U.S. Cl. ............... 128/203.15; 128/203.21
[58] Field of Search ............ 128/203.12–203.15, 128/203.21, 203.23, 207.14

[56] References Cited

U.S. PATENT DOCUMENTS

| 4,446,862 | 5/1984 | Baum et al. | 128/203.15 |
| 4,860,740 | 8/1989 | Kirk et al. | 128/203.15 |
| 5,035,237 | 7/1991 | Newell et al. | 128/203.15 |
| 5,048,514 | 9/1991 | Ramella | 128/203.15 |

FOREIGN PATENT DOCUMENTS

| 0006553 | of 1907 | United Kingdom | 128/203.21 |
| 2142246 | 1/1985 | United Kingdom | 128/203.15 |
| 2151491 | 7/1985 | United Kingdom | 128/203.15 |

*Primary Examiner*—Kimberly L. Asher
*Attorney, Agent, or Firm*—R. P. Raymond; M-E. M. Devlin; A. R. Stempel

[57] ABSTRACT

The invention relates to an inhaler for the inhalation of powdered, more particularly micronised drug preparations from capsules, the housing 10 of the inhaler containing tubular chambers 15 for receiving and holding the capsules, in a revolver magazine with an air inlet at the bottom and an air outlet 25 at the opposite end of the chamber opening into a mouthpiece 11, and a cutting device 19 with two blades 21 which are movable into the interior of the chamber in order to open the capsules near the top and bottom ends thereof.

14 Claims, 6 Drawing Sheets

POWDER INHALER HAVING MAGAZINE STORAGE AND A HINGED MOUTHPIECE

This is a continuation of application Ser. No. 08/095,029, filed Jul. 20, 1993, now abandoned which is a continuation of application Ser. No. 07/829,083, filed Mar. 12, 1992 (abandoned), which was a 371 of PCT/EP90/01336,B/14/90.

BACKGROUND OF THE INVENTION

The invention relates to an inhaler for the inhalation of powdered, more particularly micronised drug preparations from capsules, the housing of said inhaler containing a tubular chamber for accommodating and holding the capsules, the chamber having an air inlet at the base and an air outlet at the opposite end merging into an inhalation mouthpiece, and a cutting device having two blades which are movable in to the interior of the chamber in order to open the capsules near the upper and lower end thereof.

DESCRIPTION OF THE RELATED ART

U.S. Pat. No. 2,569,720 describes an inhaler having a chamber in which powdered drug preparations are distributed and through which air flows when the user inhales. To prevent the powdered drug from getting into the mouthpiece connected to the air outlet of the chamber, a seive of suitable mesh size is provided at this point. A disadvantage of this inhaler, however, is that the capsule containing the drug preparation, which usually consists of hard gelatine, has to be opened by hand before use and the powdered drug preparation—with or without the capsule—has to be introduced into the chamber; then the inhaler has to be assembled.

U.S. Pat. No. 3,918,451 relates to an inhaler, the outer housing of which has an opening which can be moved by rotation of the casing about the longitudinal axis of the housing into a position such that the chamber is freely accessible from the side and the interior of the chamber can be filled or cleaned. After the capsule has been inserted the chamber is closed by rotation of the outer casing, before two cutters of a cutting device are actuated which serve to open the capsule at top and bottom.

Moreover, U.S. Pat. No. 4,069,819 describes an inhaler, the chamber of which is supposed to be constructed so that a capsule located therein is set rotating, moving up and down and vibrating by the air flowing through, in order to ensure uniform distribution of the powdered drug.

The inhaler described in EP 0147755A2 is based on the same principle. The chamber thereof is substantially cylindrical and has an air inlet and an air outlet arranged coaxially at the bottom and top ends, respectively, the openings of which are smaller than the diameter of the capsule. This inhaler not only enables more reliable dispensing of the drug preparation with a small standard deviation, but has the additional disadvantage that, on actuation, it breaks up the powder in the capsule more satisfactorily. However, a disadvantage of this inhaler and of the other inhalers described previously is that before or after each inhalation process the single chamber has to be emptied or cleaned out, which requires the releasable or displaceable parts of the housing to be opened or taken apart beforehand.

SUMMARY OF THE INVENTION

The aim of the present invention is therefore to improve the inhaler described hereinbefore so that it is substantially easier to handle, introduction of the capsule into the tubular chamber before the next inhalation process is made easier without any great technical complexity and a capsule supply for immediate use is made available. This aim is achieved with the inhaler described in claim 1. According to the invention, instead of a single chamber in which a capsule has to be inserted or from which the capsule has to be removed, a revolving magazine is provided which has a plurality of tubular chambers each containing one capsule, which can be swung into position between the air inlet and outlet and thus forms part of the through-passage for the inhaled air. After inhalation has ended the revolving magazine is rotated further until the next chamber moves into the air throughpassage. There is no need to open the housing or laboriously change the capsule or clean the chamber. Furthermore, the device has the advantage that it can be operated by one hand.

According to a further feature of the invention the revolving magazine is releasably mounted in the inhaler housing. After the capsules present in the revolving magazine have been used up, the complete magazine can be replaced or refilled with capsules.

According to another feature of the invention the inhaler housing has an eccentrically mounted pin onto which the revolving magazine can be fitted.

In order to fix the position of the revolving magazine, it may be provided with recesses each associated with the capsule chambers for a locking bolt resiliently mounted in the inhaler housing. The recesses are arranged so that the locking bolt only engages when one of the capsule chambers is located precisely between the air inlet and outlet.

This ensures that the revolving magazine does not move out of place during the inhalation process. The resilient mounting of the locking bolt should be arranged, with respect to the spring constant, so that accidental rotation of the revolving magazine is prevented by the locking action but on the other hand when greater force is applied the revolving magazine can be rotated out of the locked position. A conical configuration on the free end of the locking bolt and correspondingly shaped recesses help with this.

The locking bolt is preferably arranged coaxially with respect to the air passage below the capsule chamber and has a through-bore which simultaneously forms the air inlet at the bottom. Preferably, the locking bolt is centrally mounted in the inhaler housing. According to a further embodiment of the invention the locking bolt is acted upon by a spring the other end of which rests on a plug releasably secured in the inhaler housing which also has a central through-bore which forms part of the air passage.

The height of the capsule chamber is determined by the length of the drug capsules. Accordingly, the blades of the cutting device, which are movable into the interior of the chamber counter to the force of a spring, are arranged in the region of the top and bottom ends of the capsule chamber. The side wall of each capsule chamber has outer radial openings facing the blades, in the region of the top and bottom ends of the chamber, or at least frangible regions which serve to allow the blades to cut through.

As already stated, the mouthpiece of the inhaler is in the form of a cap located on the lower part of the inhaler. It may be hinged to the edge of the inhaler housing so as to be pivotable about an axis extending perpendicularly with respect to the longitudinal axis of the inhaler. The mouthpiece and lower part of the inhaler housing may also, however, be secured to each other by a conventional push-fit connection. The releasability or pivotability of the two parts in any case greatly improves access in general, on the one hand to the revolving magazine and the cutting device in the lower part of the housing and, on the other hand, to the internal parts such as the seive plate and the upper part of the housing (of the cap in the form of a mouthpiece).

In order to replace the used capsules by fresh ones, the mouthpiece is flipped up or the push bit connection between the mouthpiece and the lower part of the housing is undone. The chambers of the magazine are then freely accessible, so that the empty capsules can be taken out and full ones inserted. However, the magazine may also be pulled out and, after being emptied, may be refilled with fresh capsules and put back. The device is then flipped shut or reassembled. In the upper region of the chamber, where it merges into the inhalation channel, there is a seive plate which is part of a funnel-shaped connecting member which can be fitted on to the start of the inhalation channel in such a way that the edge of the funnel engages with the seive plate in an insert plate which forms the bottom of the mouthpiece. However, the seive plate may also be replaceably clamp-fitted between the funnel edge of the connecting member and an abutment of the insert plate. It prevents a capsule from blocking the air outlet opening when the user inhales and also ensures that any fragments of capsule which may be produced are not sucked into the mouthpiece.

In a preferred embodiment, the recesses for the engagement of the locking bolt at the bottom end are provided in the base plate of the magazine concentrically with respect to the air inlet bores of the capsule chambers and are shaped like the outer shell of a flat truncated cone with its base turned outwards. In other words, these recesses are conical or funnel shaped expansions of the air inlet bores, the widened part facing the locking bolt. The sloping surfaces formed by this widening correspond substantially to the slopes on the head of the locking bolt.

In a preferred embodiment, these recesses comprise, on the base of the truncated cone surface but still in the base plate, an encircling abutment edge which serves to prevent rotation or acts as an abutment for the head of the locking bolt when the bolt is engaged in the recess. This abutment edge consequently prevents the magazine from being rotated further when the locking bolt is engaged.

According to another feature of this embodiment, the above mentioned abutment edge takes up only part or half of the circumference of the conical recess, i.e. the funnel shaped expansion, and is arranged so that it prevents the magazine from rotating in one direction when the locking bolt is engaged, but allows it to rotate in the opposite direction since the sloping wall of the funnel shaped expansion of the recess merges smoothly into the outside of the base plate.

In another preferred embodiment, only one of the recesses has an abutment edge which takes up the entire circumference of the recess, with the result that, when the locking pin is engaged in this recess, it is impossible for the magazine to rotate. This position is then regarded as the end position of a magazine in which all the capsules have been used up. In this embodiment, all the other recesses have rotation prevention means only on one side, i.e. acting in one direction, so that the magazine can only ever be rotated in the direction of insertion of a capsule chamber containing an unused capsule until the end position described above is reached, in which the magazine is totally locked in position. The user then knows that the magazine has to be loaded with fresh capsules when this last capsule has been used.

In another preferred embodiment, the blades of the cutting device are guided in a resiliently mounted sealing plate. This improves the seal between the capsule chamber in the position for inhalation and the cutting device. The spring which resets the operating button of the cutting device can be used for the resilient mounting of the sealing plate.

In another preferred embodiment, a tongue may be secured to the locking bolt, extending as far as a stop on the inside of the operating button of the cutting device when the locking bolt assumes its upper position of abutment with the revolving magazine removed. This tongue acts as a barrier to the cutting device in this position. When the magazine is inserted, the locking bolt is pressed down again and moves the barrier away from the cutting device.

Finally, in another preferred embodiment of the inhaler, a lever system is provided for actuating the cutting device. This lever system is preferably operated by an actuating button mounted on the base of the housing. The lever system may consist of a rocker arm and a toggle lever, the actuating button acting on one end of the rocker arm whilst the other end of the rocker arm presses on one end of the toggle lever, whilst the other end of the toggle lever, fixed to the cutting device, moves the cutting device forward. The rocker arm and toggle lever are preferably mounted so as to be pivotable about axis in holders secured to the housing. The actuation of the cutting device by means of this lever system may also be coupled to the rotary movement of the capsule magazine, so that the press of a button will first move a capsule chamber into the correct position and will then actuate the cutting device.

If the revolving magazine and the part of the inhaler housing adjacent to it are of N-angled construction, where N is an integer which gives the number of capsule chambers, the lateral surfaces of the inhaler housing part and the revolving magazine will advantageously be aligned when the magazine is in the correct position. It is then immediately apparent from outside whether the chamber is located in the air channel defined by the air inlet and air outlet.

According to a further feature of the invention, the inhaler has at least one cavity with openings at top and bottom below the revolving magazine.

The openings at the bottom form a connection with the air inlet at the bottom. This embodiment ensures that sufficient air reaches the air inlet during inhalation.

Preferably, the internal width of the capsule chambers is about 1.1 to 2 times as large as the capsule diameter and the total length of the capsule chamber is about 1.1 to 1.6 times as long as the capsule length, whilst the internal width must be less than the length of the capsule to prevent the capsule from tipping over. Obviously, it is only possible to clamp the capsule in the revolving magazine if the air inlet opening in the base of the cavity is smaller than the diameter of the capsule. At the top, the cavities may be open, may have an air outlet which also tapers or they may be covered by a sieve plate.

BRIEF DESCRIPTION OF THE DRAWINGS

Embodiments of the invention are shown in the drawings, wherein.

DESCRIPTION OF PREFERRED EMBODIMENTS

Figures 1A, 1B:
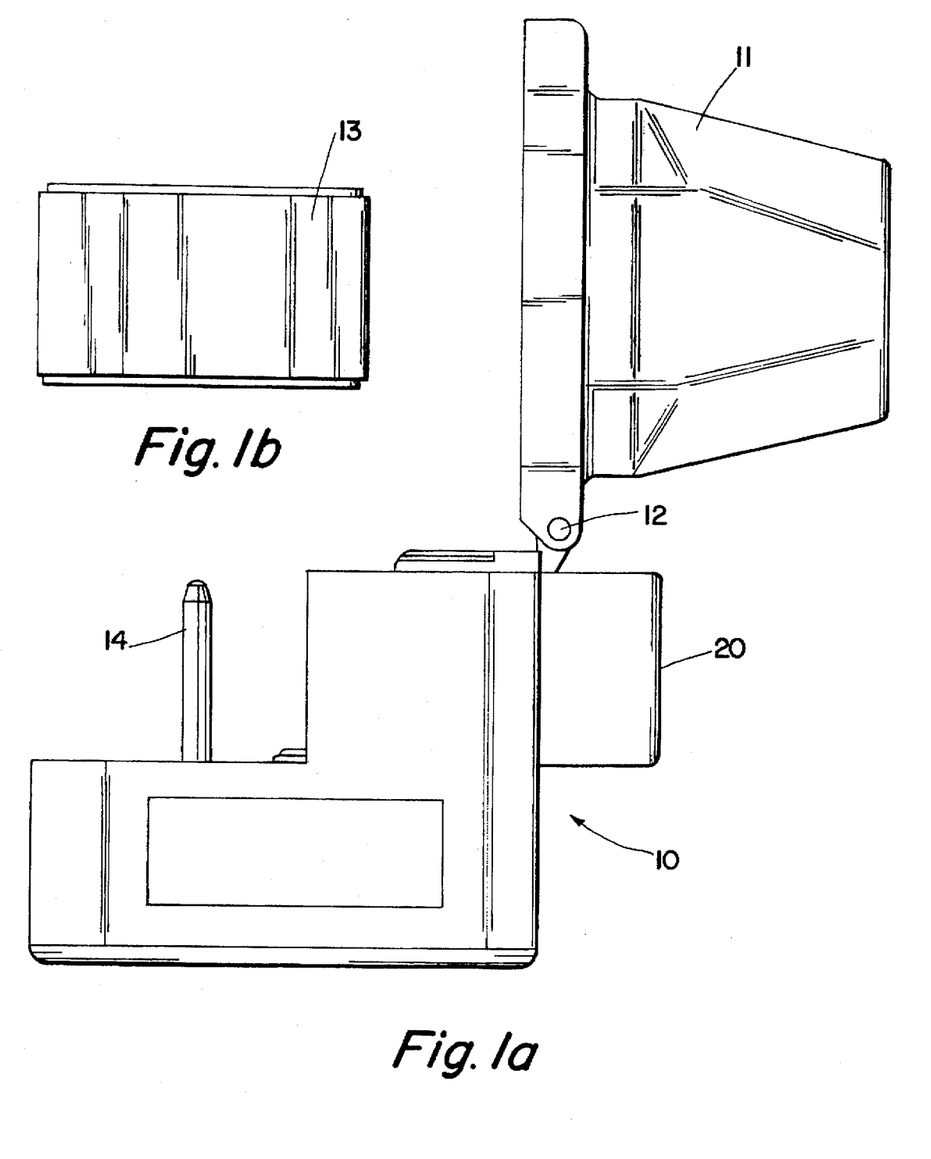
FIGS. 1a and 1b are side elevations of the inhaler housing with the mouthpiece flipped open, and the revolving magazine.
Figure 2A:
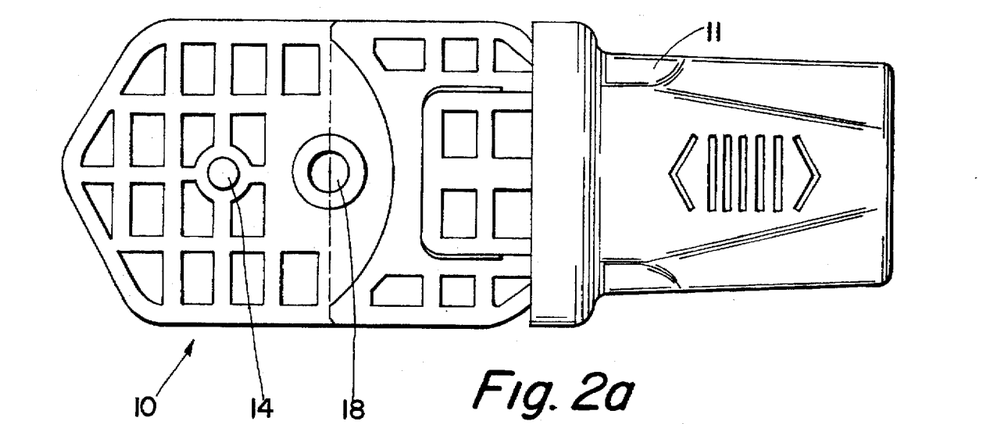
FIGS. 2a and 2b are plan views of FIG. 1.
Figure 2B:
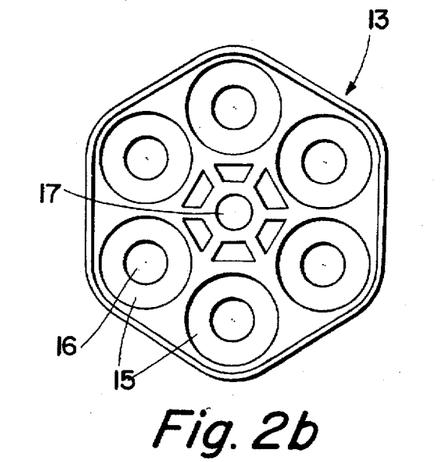

As can be seen from FIGS. 1a, 1b and 2a, the inhaler consists essentially of an inhaler housing 10 with a mouthpiece 11 which is laterally hinged to the upper edge of the inhaler housing so as to be pivotable about an axis 12. Capsules are received in chambers 15, 15'(FIG. 4) in a revolving magazine 13 which can be placed on a pin 14 eccentrically mounted on the inhaler housing 10. After the revolving magazine 13 has been fitted in position, the mouthpiece 11 is moved into its normal position, as a cap on the housing; the inhaler is ready for use. As FIG. 2b shows, the revolving magazine 13 has six chambers 15 for receiving the capsules (not shown). The bottom of each chamber 15 has an air inlet bore 16. The revolving magazine 13 also has an axial guide 17 for the pin 14.

As can be seen from FIG. 3, the inhaler has, adjoining the chamber 15 arranged below the inhalation channel 33, a cutting device 19 which is operable by means of an actuating button 20. This cutting device 19 has two blades 21 which can be introduced radially into the top or bottom part of said chamber 15, the outer wall of the revolving magazine having perforations or frangible areas 22 situated at corresponding points to make it easier for the blades 21 to pass through. The blades 21 serve to open the capsule located in a chamber 15, near the upper or lower end of the capsule. The revolving magazine 13 also has, underneath the bores 16, conical recesses 23 in which a locking bolt 24 can engage as soon as a chamber 15 is coaxial with the air inlet 18 or inhalation channel 33 of the inhaler housing.

The locking bolt is also of conical construction at its end which engages in the recess 23. At the opposite end it is acted upon by a spring 26 which bears on a plug 27 releasably secured in the inhaler housing. This plug, like the locking bolt, has a central through-bore which serves as an air inlet 18. The internal width of the chamber 15 is about 1.1 to 2 times as great as the capsule diameter and the length of the capsule chamber (including the air outlet 25) is approximately 1.1 to 1.6 times the capsule length. However, the internal width of the chamber is less than the length of the capsule.

In order to prepare the inhaler, the revolving magazine 13 is inserted and one of the chambers 15 is moved by rotation of the revolving magazine into a position where the bore 16 at the bottom or the conical recess 23 is aligned so as to be coaxial with the air inlet opening 18. The adjustment of the chamber 15 is made easier by the engagement of the locking bolt 24 in the recess 23. After the bolt has clicked into place the air inlet opening 18 and the bottom opening 16 of the chamber 15 are in alignment. The cap of the capsule is located on the bottom opening 16 and closes it off. By actuating the operating button 20 counter to the force of a spring 28, the blades 21 are moved radially towards the chamber 15, and first of all they pass through the frangible regions 22 or enter into suitable openings provided in the side wall of the revolving magazine and finally they open the capsule at top and bottom close to the ends thereof. The hemispherical caps of the capsules should not be destroyed, as they are supposed to act as a sort of valve.

In order to facilitate the severing of the frangible regions 22, the corresponding places are preferably offset so that the upper blade has to pass through the frangible region before the lower blade reaches it.

If air is then taken in through the mouthpiece 11, the air flowing into the chamber 15 from the openings 29 at the bottom of the housing 10 and from the inlet 18 cause the capsule to vibrate violently, whips up the powder in the capsule, becomes mixed up with the powder and is finally inhaled. The mouthpiece 11 is generally of tubular construction but may also be adapted to fit the shape of the mouth and be of flattened construction. As a variant of this embodiment, it is also possible to have axial mouthpiece arrangements or arrangements which are offset at an angle to the axis of the chamber of laterally with respect to the axis of the chamber.

Figure 3:
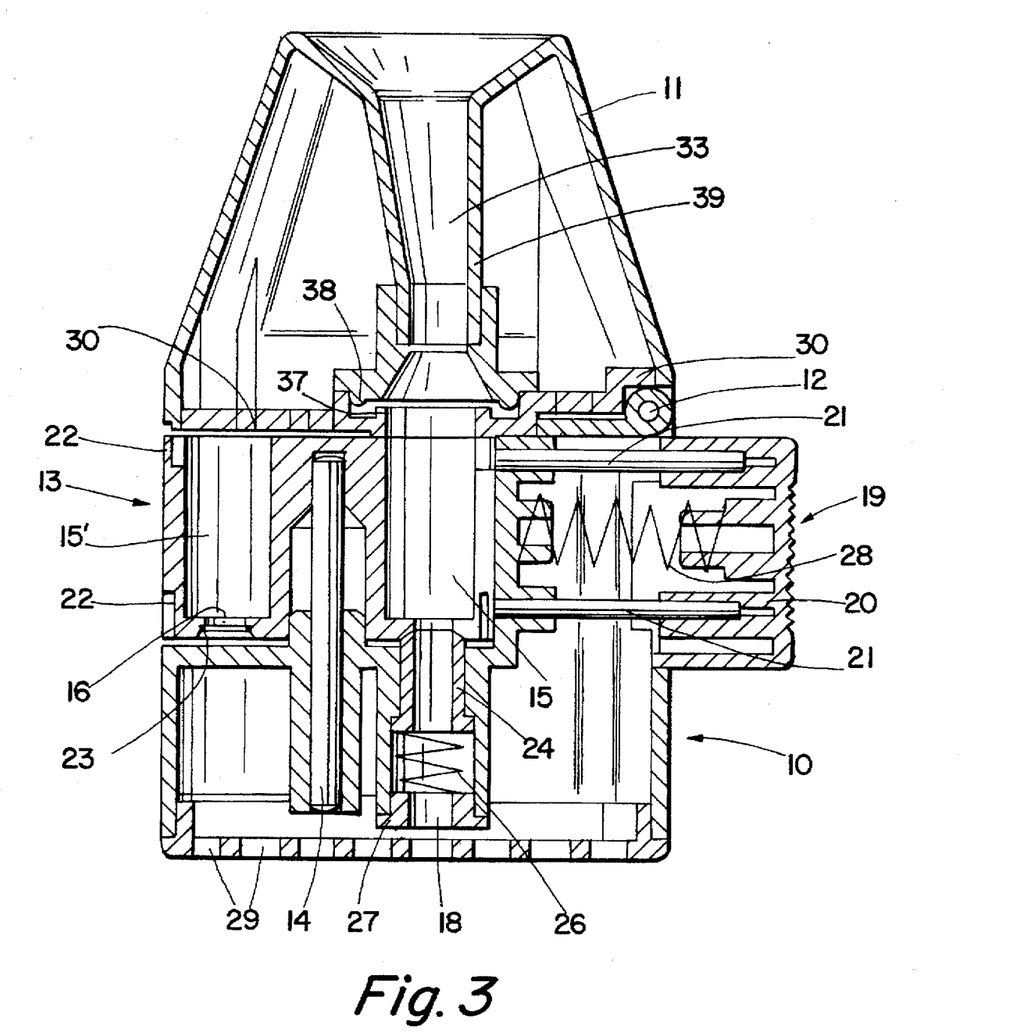
FIG. 3 is a section through a first embodiment of the inhaler.
Figure 4:
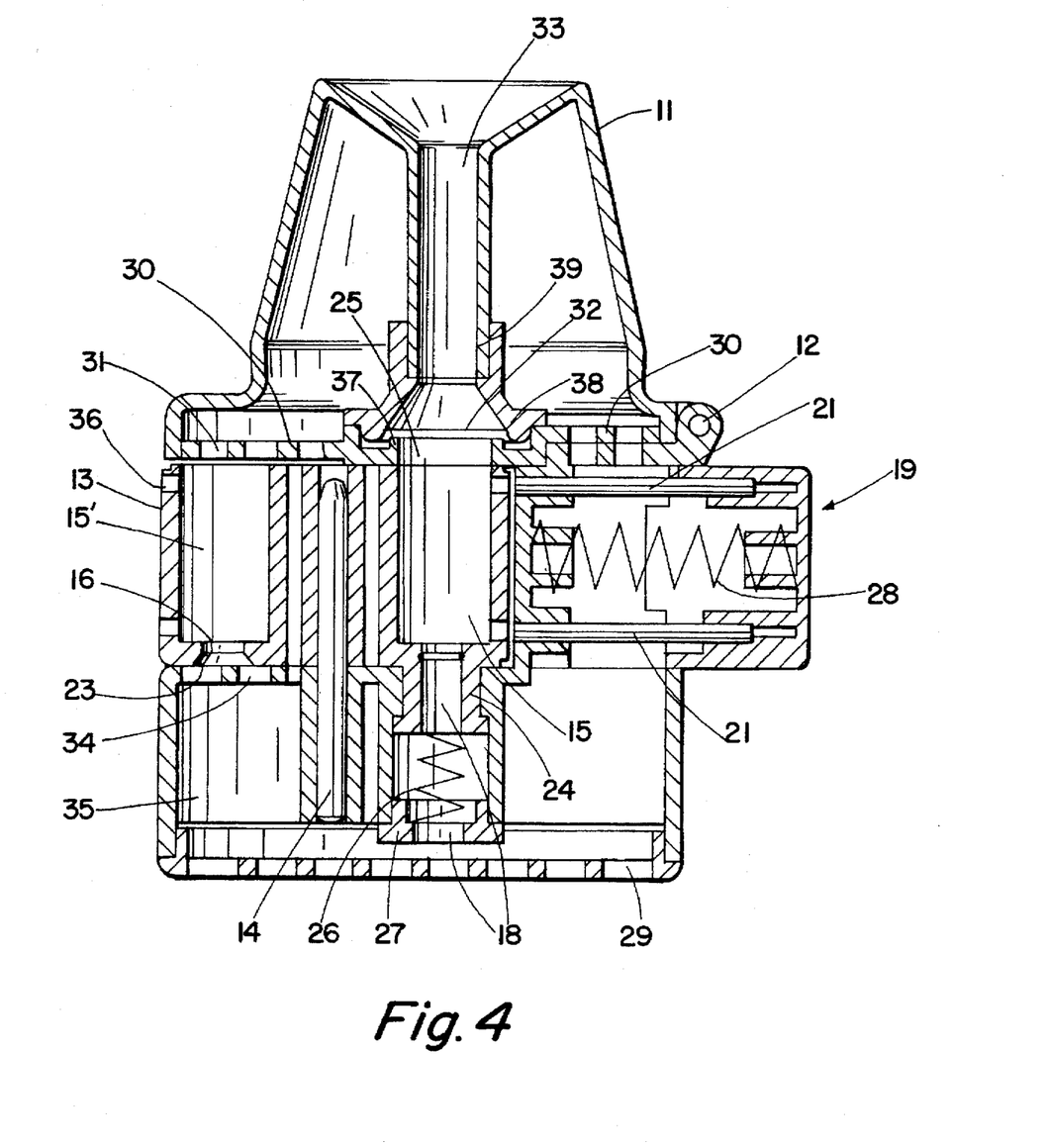
FIG. 4 is a section through a second embodiment of the inhale.

Whereas, in the embodiment shown in FIG. 3, the mouthpiece or cap 11 is provided at the bottom with a substantially closed insert plate 30, the insert plate 30 according to FIG. 4 has openings 31. Furthermore, in the embodiment shown in FIG. 4, the start of the inhalation channel 33 is covered with a seive 32 which prevents the capsule or fragments thereof from entering the inhalation channel 33 in the mouthpiece during inhalation. As an alternative, wall projections may be provided at this point to hold the capsule back. The sieve plate 32 is preferably arranged in the centre of the insert plate 30, and is advantageously clamped between a stop 37 of the plate 30 which comprises the air passage and the edge of a funnel shaped connecting member 38, which is fitted on the start 39 of the inhalation channel 33 in such a way that the funnel edge faces the insert plate 30 and engages therewith. The projections provided as an alternative may also be arranged at this point.

Furthermore, the inhaler housing 10 may have openings 34 in the side facing the revolving magazine 30 or the bores 16 thereof, these openings 34 terminating in an annular cavity 35 in the housing which is able to communicate with the air inlet 18 at the bottom.

Figure 2C:
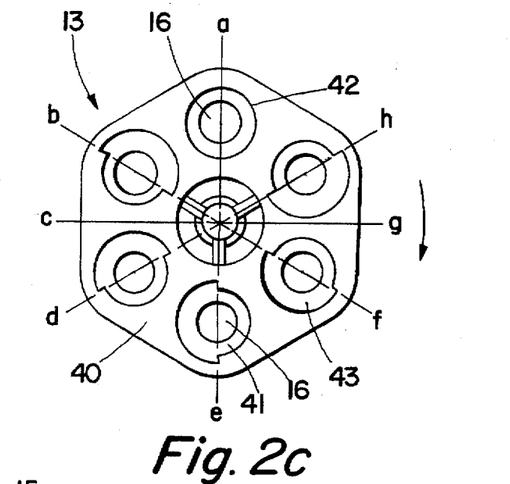
FIG. 2c is a view of the base plate of the revolving magazine.
Figure 2D:
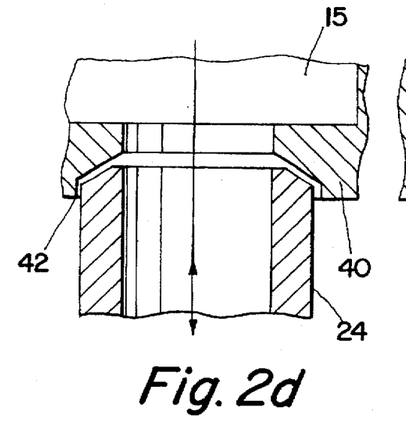
FIGS. 2d and 2e are enlarged views of cut-out portions of the engagement point of the locking bolt.
Figure 2E:
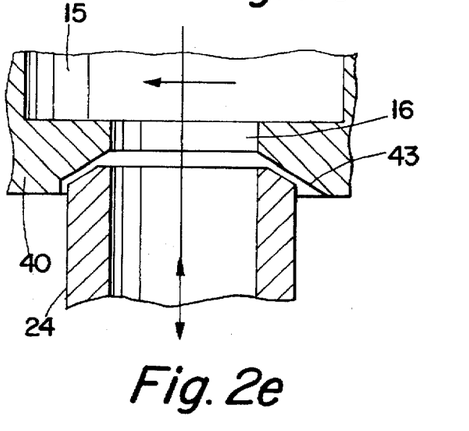

FIGS. 2c, d and e show a preferred embodiment of the locking means for the revolving magazine. FIG. 2c shows a view of the base plate 40 of the revolving magazine 13. FIGS. 2d and 2e show enlarged partial sections through the position of engagement of the locking bolt 24 in the base plate 40 of the preferred embodiment of the base plate 40 according to FIG. 2c. As can be seen from FIG. 2c, a concentric surface or slope designated 43 and 41 is arranged around each bore 16. This surface is supposed to be the exit contour of the funnel-shaped widening of the bore 16 in the base plate 40. FIG. 2e shows the particular configuration of this exit contour more clearly. On the one hand it has a slope 43 which merges smoothly with the surface of the base plate 40 and on the opposite side it has an edge 42 (FIG. 2d) which describes a smaller radius. The edge 42 constitutes a stop for the locking bolt 24 and prevents the magazine from rotating against the edge 42. However, the magazine may also readily be rotated in the direction of the slopes 43 as shown in FIG. 2c. Also as shown in FIG. 2c, the abutment edges 42 extending over half the circumference of the conical expansion are arranged in the same direction, i.e. they prevent the magazine from rotating in the same direction and allow it to rotate only in the direction of the arrow over the slopes 43, which are shown with a larger diameter in FIG. 2c. The positions shown in FIG. 2c are designed a to h. The conical recess in position a has the special feature of having a stop edge 42 which extends over the entire circumference. In other words, in position a, the locking bolt 24 would not allow the magazine to rotate in any direction. Consequently, for the user, this position is the end position in which all the capsules in the magazine have been used up and have to be replaced by fresh capsules. In positions b to h the recesses are constructed in the manner just described, in which the magazine can rotate only in the direction of the arrow. This prevents any capsule which has already been used from being returned to the inhalation chamber.

Figure 5:
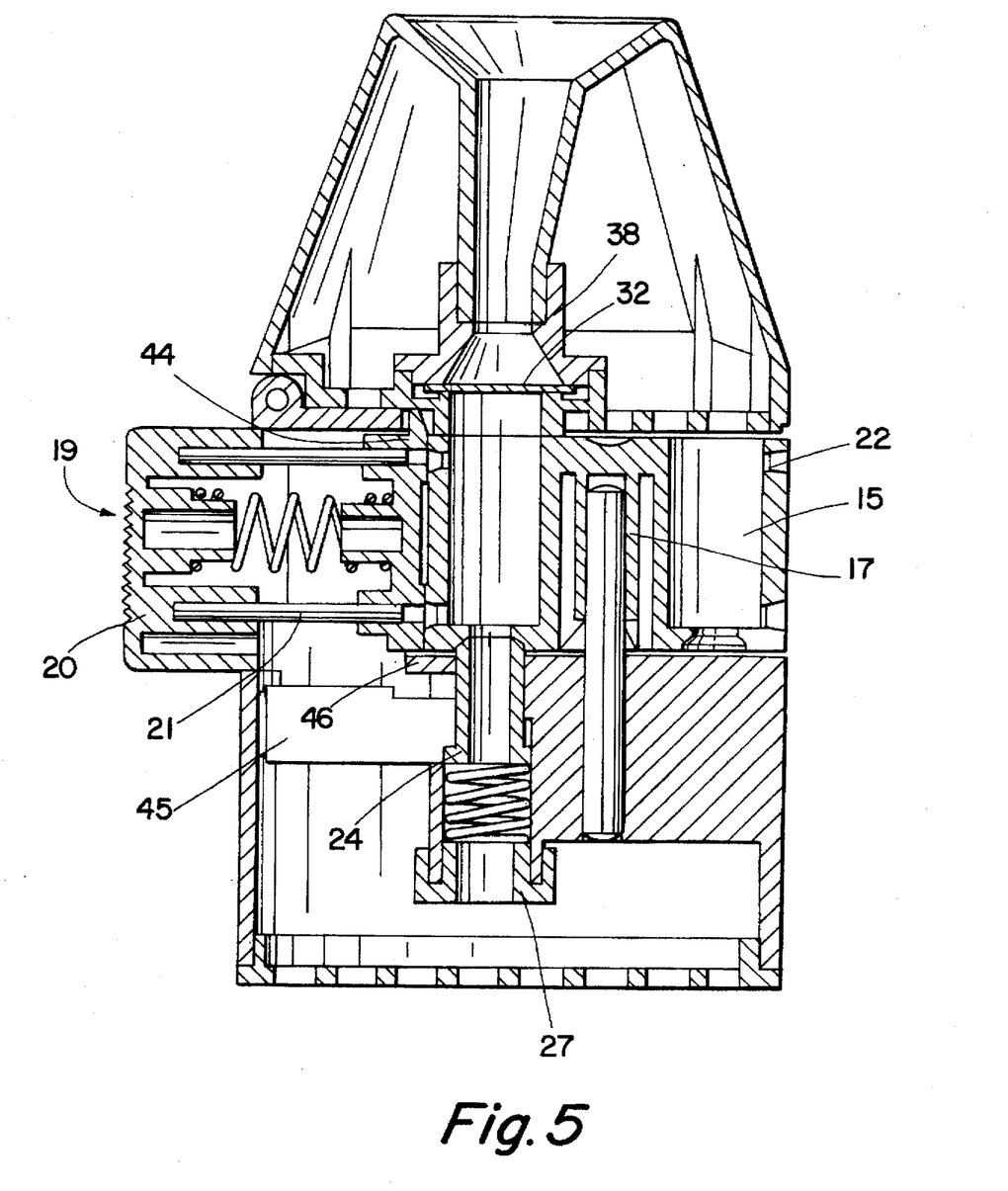
FIG. 5 is a section through a third embodiment of the inhaler.

FIG. 5 shows an embodiment of the inhaler with a resiliently mounted sealing plate 44 for the blades 21 and a barrier 45 for the operating button 20. The guiding of the blades 21 in a sealing plate 44 which is separate and detached from the housing improves and aids the sealing off of the space containing the cutting mechanism from the inhalation chamber. The sealing plate 44 can be pressed against the sealing surfaces by means of the same spring which causes the operating button 20 of the cutting device 19 to be reset.

The barrier 45 for the operating button 20 is preferably connected to the locking bolt 24. It performs its blocking action when the locking bolt 24 has reached its upper stop position against the stop 46, with the revolving magazine 13 removed. When the revolving magazine is put in, the locking bolt 24 is pressed down again and the tongue 45 is also moved out of the blocking area.

Figure 6:
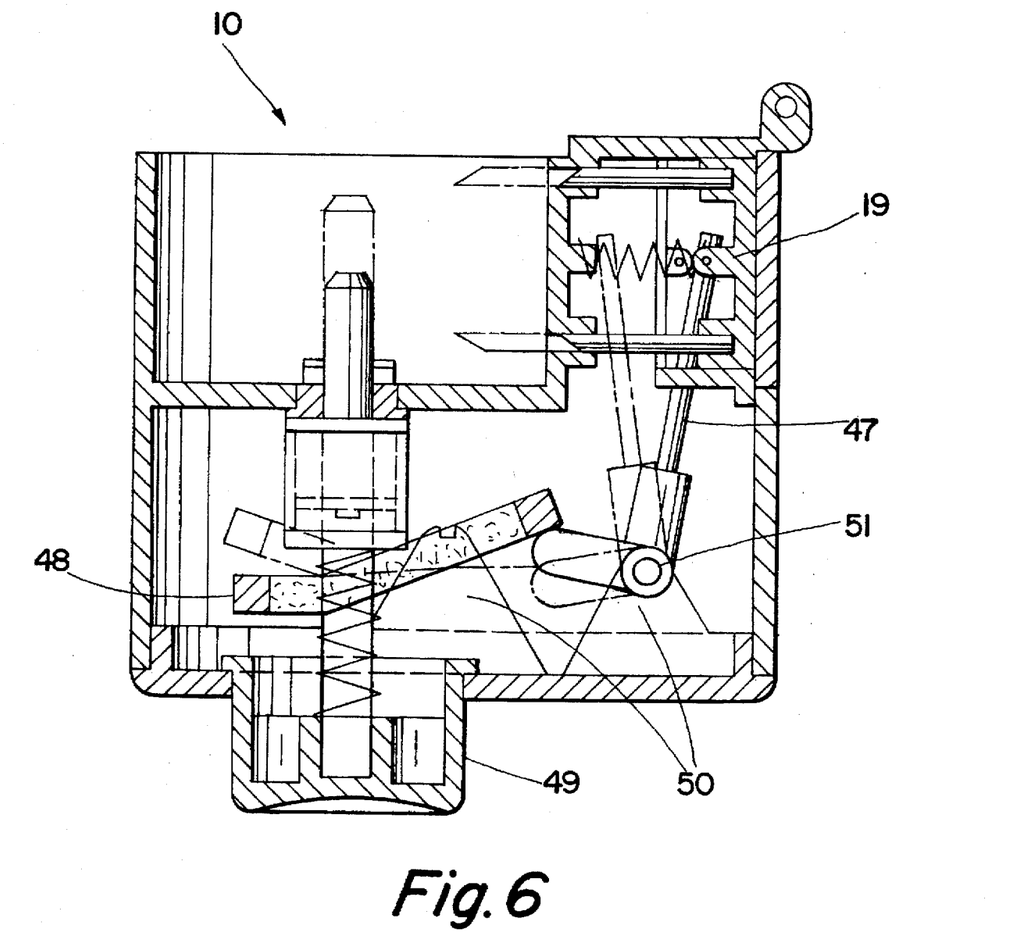
FIG. 6 is a section through the lower part of a fourth embodiment of the inhaler.

The embodiment shown in FIG. 6 shows a lever system 47, 48 for actuating the cutting device 19 by means of an operating button 49 mounted in the base of the housing. The first lever 48, in the form of a rocker arm, presses on the short end of the toggle lever 47 when the operating button 49 is pushed upwards, whilst the long end of the toggle lever 47 acts on the cutting device 19. The rocker arm 48 and toggle lever 47 in the embodiment shown are mounted in holders 50 so as to be pivotable about the axis 51. This embodiment can also be arranged so that actuation of the button 49 simultaneously rotates the capsule magazine 13 and then activates the cutting device 19.

We claim:

1. An inhaler for the inhalation of powdered drug preparations contained in capsules which inhaler has a housing having a tubular chamber for receiving the capsules, which chamber has an air inlet at one end thereof, and an air outlet at the opposite end thereof merging into an inhalation mouthpiece, which chamber is also arranged substantially centrally in the housing, and a cutting device having two blades which are movable in the interior of the tubular chamber for opening the capsules in the region of the top and bottom ends thereof, the improvement which comprises a revolving magazine rotatably mounted on a pin with in the tubular chamber which magazine has a plurality of tubular-shaped capsule chambers, each of which can be loaded with a capsule, the longitudinal axis of said tubular-shaped capsule chambers being parallel to the axis of the inhaler and which are arranged together with the revolving magazine in such a way that they can be pivoted into position between the air inlet and the air outlet and thus form a coaxial unit and the inhalation mouthpiece is hinged at the edge of the housing so as to be pivotable about an axis extending perpendicularly to the longitudinal axis of the inhaler.

2. The inhaler according to claim 1 further characterized in that the revolving magazine has recesses associated with each of the tubular-shaped capsule chambers and a locking bolt resiliently mounted in the housing such that the recesses are arranged so that the locking bolt engages if one of the tubular-shaped capsule chambers forms a coaxial unit with the air inlet and outlet respectively.

3. The inhaler according to claim 2 further characterized in that the locking bolt is of conical construction.

4. The inhaler according to claim 2 further characterized in that the recesses are provided at the bottom in the base plate of the revolving magazine concentrically with air inlet bores in the tubular-shaped capsule chambers, and are shaped in the manner of the exterior of a flat truncated cone with its base facing outwards.

5. The inhaler according to claim 4 further characterized in that one of the recesses has an encircling abutment edge on the base of the truncated cone shell, but still in the base plate, and all the other recesses have the said abutment edge over at most half the circumference of the base of the truncated cone shell, said abutment edges acting in the same direction.

6. The inhaler according to claim 2 characterized in that the locking bolt has a through-bore which forms the air inlet at the bottom, the locking bolt being acted upon by a spring, the other end of which abuts on a plug releasably secured in the inhaler housing, the plug also having a central through bore.

7. The inhaler according to claim 2, characterized in that the cutting device can be actuated by means of a lever system and an operating button provided in the base of the housing.

8. The inhaler according claims 7, characterized in that the operating button is operatively connected to one end of a rocker arm, the other end of which acts on one end of a toggle lever, the other end of which is connected to the cutting device.

9. The inhaler according to claim 7, characterized in that, secured to the locking bolt, there is a tongue which extends as far as a stop on the inside of the operating button, when the locking bolt assumes its upper position of abutment, with the revolving magazine removed, so that the tongue in this position acts as a barrier for the cutting device.

10. The inhaler according to claim 1 characterized in that the walls of the chamber have frangible regions for the passage of the blades of the cutting device, the blades being arranged so that one blade enters near the bottom of the chamber and a second blade enters near the top end of the capsule in the chamber, whilst the frangible regions may be offset from each other so that they are pierced one after the other.

11. The inhaler according to claim 1 characterized in that the blades of the cutting device are guided in a resiliently mounted sealing plate.

12. The inhaler according to claim 1 characterized in that the mouthpiece is hinged to the edge of the inhaler housing so as to be pivotable about an axis extending perpendicularly to the longitudinal axis of the inhaler.

13. The inhaler according to claim 1 characterized in that, in the upper region of the chamber, where it merges with the inhalation mouthpiece, a sieve plate is provided which is replaceable clamped between the funnel edge of the connecting member and a stop of the insert plate.

14. The inhaler according to claim 1, characterized in that the internal width of the tubular-shaped capsule chamber is about 1.1 to 2 times as great as the capsule diameter and the overall length of the tubular-shaped capsule chamber is about 1.1 to 1.6 times the capsule length.

* * * * *